US011116880B2

(12) United States Patent
Quackenbush

(10) Patent No.: US 11,116,880 B2
(45) Date of Patent: Sep. 14, 2021

(54) MANUAL BREAST PUMP

(71) Applicant: MOMI BRANDS, INC., Winston Salem, NC (US)

(72) Inventor: Carr Lane Quackenbush, Monson, MA (US)

(73) Assignee: Momi Brands, Inc., Winston Salem, NC (US)

( * ) Notice: Subject to any disclaimer, the term of this patent is extended or adjusted under 35 U.S.C. 154(b) by 0 days.

(21) Appl. No.: 17/036,605

(22) Filed: Sep. 29, 2020

(65) Prior Publication Data

US 2021/0121616 A1   Apr. 29, 2021

Related U.S. Application Data

(60) Provisional application No. 62/927,365, filed on Oct. 29, 2019.

(51) Int. Cl.
*A61M 1/06* (2006.01)
*A61J 9/00* (2006.01)
*A61M 39/24* (2006.01)

(52) U.S. Cl.
CPC ............... *A61M 1/064* (2014.02); *A61J 9/00* (2013.01); *A61M 39/24* (2013.01)

(58) Field of Classification Search
CPC .............. A61M 1/0037; A61M 1/0072; A61M 2205/50; A61M 2205/502;
(Continued)

(56) References Cited

U.S. PATENT DOCUMENTS 2,864,628 A    12/1958  Edleson
4,263,912 A *   4/1981  Adams ................... A61M 1/06
                                                  604/75
(Continued)

FOREIGN PATENT DOCUMENTS

CA    2240268 A1   12/1999
WO   2004/058330 A1    7/2004

OTHER PUBLICATIONS

International Search Report for International Application No. PCT/US2017/68633 dated Mar. 19, 2018.
(Continued)

*Primary Examiner* — Scott J Medway
(74) *Attorney, Agent, or Firm* — Lathrop GPM LLP; WM. Tucker Griffith

(57) ABSTRACT

A manual pump apparatus and method for extracting breastmilk is disclosed. A pump head comprises a funnel-shaped breast shield portion and a neck portion leading to a collection container. A deformable elastic component is sealed within an opening formed in the neck portion and manipulated by a mechanical actuation device to engage the user's nipple within the pump head to simulate the suckling of an infant and to compress the nipple to control edema. The deformable elastic component is configured to move into the interior volume of the neck portion under an applied pressure such that the deformable elastic component compresses the nipple to control nipple edema. The deformable elastic component is also configured to move away from the axial center of the neck portion under an applied pressure to create a volume to create suction and extract breastmilk in a manner that closely replicates the suckling of an infant.

20 Claims, 6 Drawing Sheets

(58) Field of Classification Search
CPC .......... A61M 2209/088; A61M 1/0031; A61M 1/06; A61M 2205/3344
See application file for complete search history.

(56) References Cited

U.S. PATENT DOCUMENTS

| | | | |
|---|---|---|---|
| 4,607,596 A | 8/1986 | Whittlestone et al. | |
| 4,857,051 A | 8/1989 | Larsson | |
| 6,273,868 B1* | 8/2001 | Nordvik | A61M 1/064 |
| | | | 604/74 |
| 6,673,036 B1 | 1/2004 | Britto | |
| 6,749,582 B2 | 6/2004 | Britto et al. | |
| 6,840,918 B1 | 1/2005 | Britto et al. | |
| 6,887,210 B2 | 5/2005 | Quay | |
| 7,101,350 B2* | 9/2006 | Ytteborg | A61M 1/064 |
| | | | 604/74 |
| 7,875,000 B2 | 1/2011 | Krebs et al. | |
| 7,988,661 B2 | 8/2011 | Silver et al. | |
| 8,052,635 B1 | 11/2011 | Kelly | |
| 8,118,772 B2 | 2/2012 | Dao et al. | |
| 8,216,179 B2 | 7/2012 | Bosshard et al. | |
| 8,961,454 B2 | 2/2015 | Chen | |
| 10,016,548 B1 | 7/2018 | Quackenbush | |
| 10,286,130 B2 | 5/2019 | Quackenbush | |
| 10,485,908 B2* | 11/2019 | Alvarez | A61M 1/064 |
| 10,806,837 B2 | 10/2020 | Quackenbush | |
| 2004/0158199 A1 | 8/2004 | McKendry et al. | |
| 2005/0234370 A1* | 10/2005 | Beal | A61H 9/0078 |
| | | | 601/15 |
| 2006/0106334 A1 | 5/2006 | Jordan | |
| 2010/0130921 A1* | 5/2010 | Kobayashi | A61M 1/062 |
| | | | 604/74 |
| 2014/0121593 A1 | 5/2014 | Felber et al. | |
| 2014/0288466 A1 | 9/2014 | Alvarez et al. | |
| 2014/0378946 A1 | 12/2014 | Thompson | |
| 2015/0065994 A1 | 3/2015 | Fridman et al. | |
| 2016/0000982 A1 | 1/2016 | Alvarez et al. | |
| 2016/0058928 A1 | 3/2016 | Nowroozi et al. | |
| 2016/0206794 A1 | 7/2016 | Makower et al. | |
| 2017/0312409 A1* | 11/2017 | Alvarez | A61M 1/062 |
| 2019/0240386 A1 | 8/2019 | Larsson | |

OTHER PUBLICATIONS

Written Opinion for International Application No. PCT/US2017/68633 dated Mar. 19, 2018.

N.P. Aleekseev, E.V. Omel'yanyuk, and N.E. Talalaeva, Dynamics of milk ejection reflexes accompanying continuous rhythmic stimulation of the areola--nipple complex of the mammary gland, 2000, Ros. Fiziol, Zhum, im. I.M. Sechenova, vol. 86, No. 6, pp. 711-719 (Year: 2000).

* cited by examiner

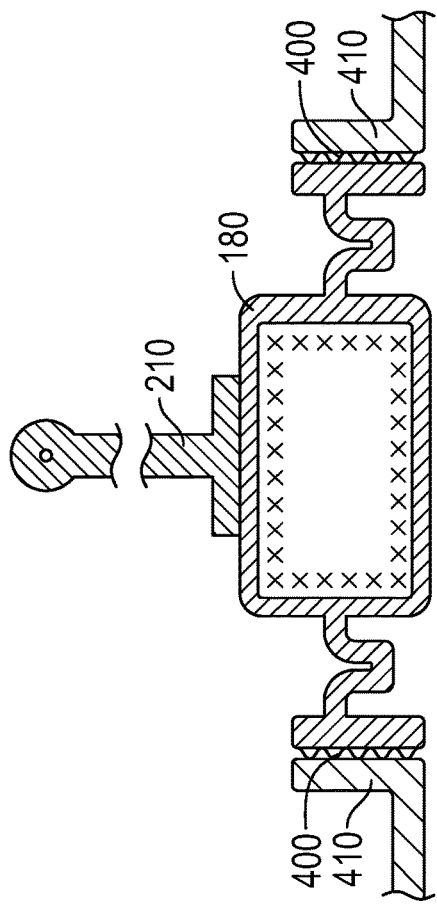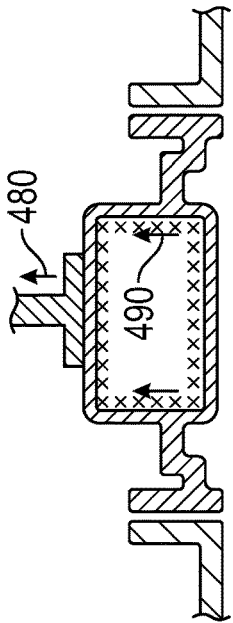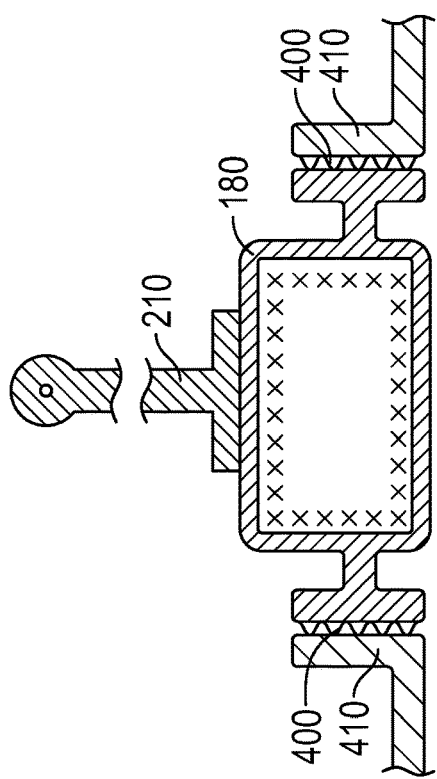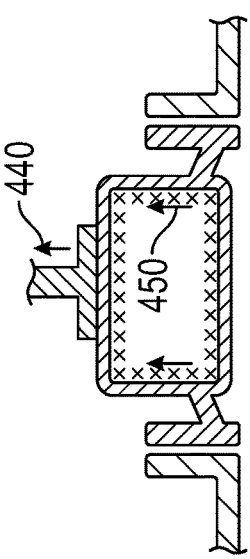

MANUAL BREAST PUMP

CROSS-REFERENCE TO RELATED APPLICATION

This application claims the benefit of U.S. Provisional Application No. 62/927,365, filed Oct. 29, 2019, which is incorporated herein by reference in its entirety.

FIELD OF INVENTION

The present invention relates generally to milking and breast pump devices and, more particularly, to breast pumps, and specifically, manual breast pumps, for lactating females designed to mimic the natural suckling action of an infant during breast-feeding.

BACKGROUND OF THE INVENTION

Newborns and infants experience immediate and long-term benefits from breast milk feeding that are well documented. (See Cunningham A. S., Jelliffe D. B., Jelliffe E. F., Breast feeding and health in the 1980s: a global epidemiological review. Journal of Pediatrics. 1991, 118: 659-666). These benefits include providing protection against many illnesses caused by allergies, bacteria and viruses, such as stomach viruses, respiratory illnesses, ear infections, meningitis and the like. (See Fallot M. E., Boyd J. L., Oski F. A., Breast-feeding reduces incidence of hospital admissions for infection in infants. Pediatrics. 1980, 65:1121-1124). Breast milk feeding also may increase intelligence and fight obesity.

Nursing mothers may desire to impart the above-noted benefits of breast milk to their infant when the two are separated. Additionally, traditional nursing may not be possible or convenient at all times and locations. Thus, to extract breast milk to later feed to the infant, nursing mothers can use a breast pump. The extracted breast-milk can be fed to the infant using a bottle fitted with an artificial teat.

All current commercial breast pumps, including both manual and electric breast pumps, use vacuum (i.e., negative air pressure) applied to the mother's breasts to extract milk. The use of vacuum to extract breast milk is completely different than the natural suckling action of the infant, in which the infant's mouth is filled only with liquid, and no air. Worse still, breast pumps using only vacuum can cause significant pain to the mother, or even edema in nursing mothers, which inhibits the collection and even production of breastmilk.

Therefore, it is desirous to provide an improved approach to breast pumps that more closely mimic the natural suckling action of the infant and does not cause pain or edema.

SUMMARY OF THE INVENTION

The present invention provides a manual breast pump that more closely mirrors the natural suckling action of an infant, and, as a result, improves upon the collection of breastmilk generally associated with breast pumps.

According to embodiments of the present invention, a device for extracting breastmilk from a breast, such as a breast pump, comprises an external shell including a funnel-shaped portion configured to receive and seal against the breast; a neck portion extending from the funnel-shaped portion and defining a proximal end and a distal end, said neck portion being adapted to receive and position a nipple of the breast, and a feed channel defined at the distal end of the neck portion. A deformable elastic component is sealed into the neck portion with a first surface facing an interior of the neck portion and a second surface facing away from the interior of the neck portion. The first surface of the deformable elastic component is configured to deform into the interior volume of the neck portion when pressure is applied to the exterior second surface of the deformable elastic component in a direction toward an axial center of the neck portion such that the first surface of the deformable elastic component compresses the nipple against an opposing interior solid surface of the neck portion to control nipple edema. The first surface of the deformable elastic component is also configured to deform away from the axial center of the neck portion when pressure is applied to the exterior second surface of the deformable elastic component in a direction away from the axial center of the neck portion and thus to create a volume within the neck portion, external to the deformable elastic component, around and in front of the nipple, to create suction and extract breast milk.

In preferred embodiments, the neck portion includes an opening in which the deformable elastic component is seated and sealed. As positioned in said opening, the first surface of the deformable elastic component preferably extends across the opening. Still further, the deformable elastic component is preferably hermetically sealed into the neck portion. In alternate embodiments, the deformable elastic component can be detachable from the pump head, but still preferably sealed when attached.

In embodiments of the present invention, the deformable elastic component comprises a single unitary, hermetic unit. In alternate embodiments, the deformable elastic component is composed of multiple components, sealed together, and configured to function as a single unitary, hermetic unit. The deformable elastic component can comprise a single impermeable polymeric membrane, bladder, a hollow capsule, or the like, sealingly mounted relative to an opening in the neck portion of the external shell. The deformable elastic component can be filled with air, a gas, a liquid, a gel, or the like, and be manipulated under pressure using a mechanical actuator means, such as a handle and pushrod combination.

According another aspect of the present invention, a milking machine comprises an external shell including a funnel-shaped portion configured to receive and seal against a breast; a neck portion extending from the funnel-shaped portion and defining a proximal end and a distal end, said neck portion being adapted to receive and position a nipple of the breast; and a feed channel defined at the distal end of the neck portion. A deformable elastic component is sealed into the neck portion with a first surface facing an interior of the neck portion and a second surface facing away from the interior of the neck portion. A mechanical actuation device, controlled by the user, is operatively connected to the second surface of the deformable elastic component. The first surface of the deformable elastic component is configured to deform into the interior volume of the neck portion when pressure is applied to the exterior second surface of the deformable elastic component in a direction toward an axial center of the neck portion such that the first surface of the deformable elastic component compresses the nipple against an opposing interior solid surface of the neck portion to control nipple edema. The first surface of the deformable elastic component is also configured to deform away from the axial center of the neck portion when pressure is applied to the exterior second surface of the deformable elastic component in a direction away from the axial center of the neck portion and thus to create a volume within the neck portion, external to the deformable elastic component, around and in front of the nipple, to create suction and extract breast milk.

These and other objects, features and advantages of the present invention will become apparent in light of the detailed description of embodiments thereof, and as illustrated in the accompanying drawings.

BRIEF DESCRIPTION OF THE DRAWINGS

FIGS. 3A-3F show cross-sectional views of a portion of a breast pump head, having the same features as in FIG. 1 in accordance with embodiments of the present invention, containing a flexible element disposed and hermetically bonded between the pocket in the neck portion of the breast pump head and the deformable unitary elastic capsule to provide increased displacement of the deformable elastic capsule relative to the neck portion beyond simple deformation of its shape.

DETAILED DESCRIPTION OF PREFERRED EMBODIMENTS

The following descriptions of the figures will convey details of construction and operation of a manual breast pump in accordance with the present invention.

As described herein, the terms "proximal" and "distal" are used in their medical sense and directionally with respect to the user. Thus, "distal" is farthest from the user, and the "distal portion" of the nipple is the portion drawn deepest into the pump. "Bottom," "lower" or "down" are generally used in reference to the orientation illustrated in the figures, and signify a direction toward the breastmilk collection container. Conversely, "top," "upper" or "up" refer to a direction away from the breastmilk collection container.

Figure 1:
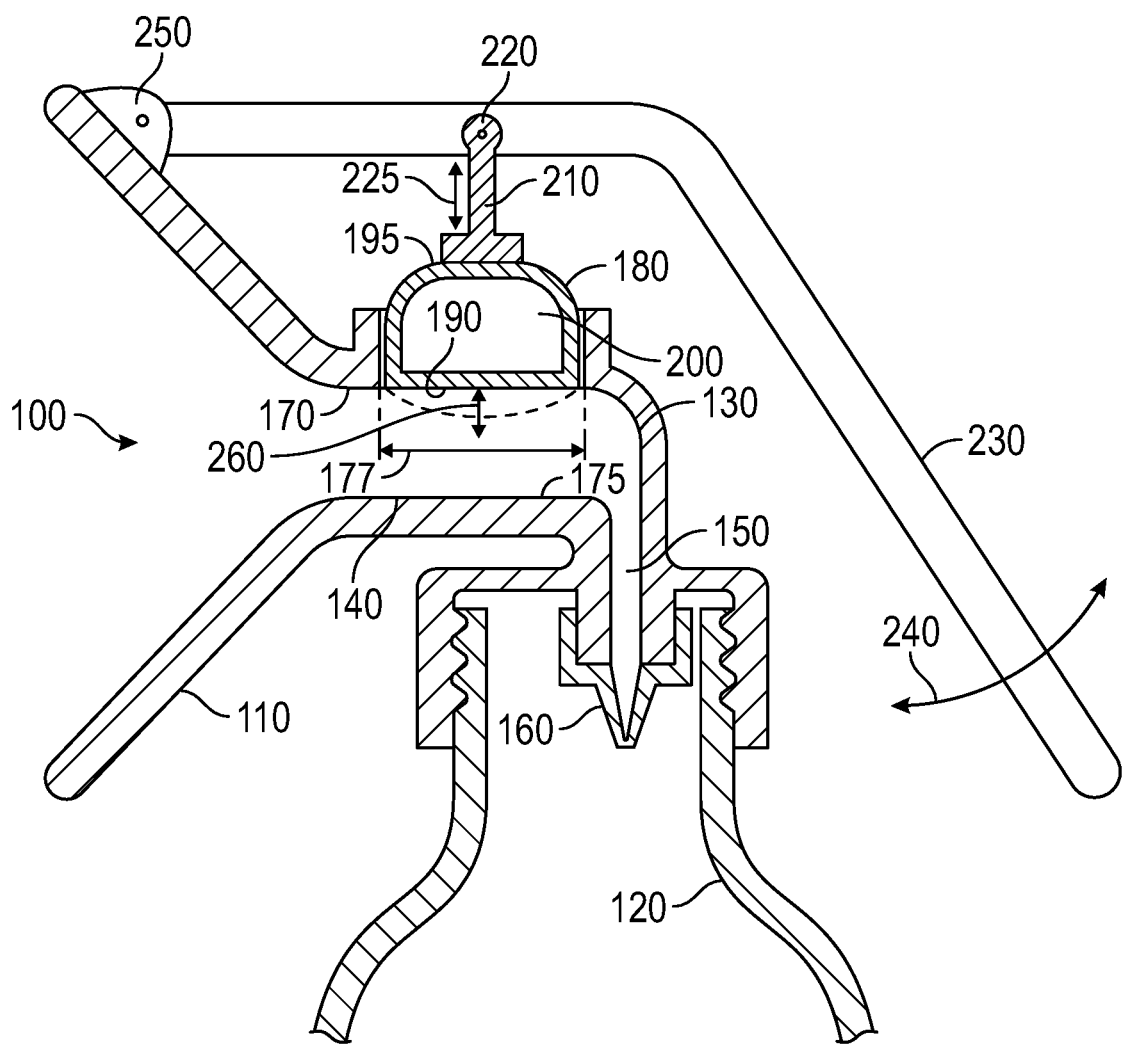
FIG. 1 shows a cross-sectional view of a breast pump head in accordance with an embodiment of the present invention, including a funnel-shaped breast shield section, a neck portion, a deformable unitary elastic capsule bonded at its sides into a pocket in the neck portion, a one-way valve, a breastmilk collection container, and further having a handle operatively connected to the exterior top surface of the deformable unitary elastic capsule by a pushrod.

Referring to FIG. 1, an assembled breast pump head for extracting breastmilk in accordance with the present invention is generally designated as reference numeral 100. The breast pump head 100 generally comprising an external shell that includes a funnel-shaped breast shield portion 110 configured to receive and seal against a breast (not shown in FIG. 1). As illustrated, the funnel-shaped breast shield portion 110 narrows and transitions to a roughly cylindrical and hollow neck portion 140 defining a proximal end located adjacent to the funnel-shaped breast shield portion 110 and a distal end positioned away from the funnel-shaped breast shield portion 110. The neck portion 140 is adapted to receive and position a nipple of the breast for extraction of breastmilk. Preferably, the distal end of the neck portion 140 is closed off, for example, by a distally curved portion 130, so that a channel is formed within the pump head 100 which feeds, at the distal end of the neck portion 140, to a feed channel 150. In operation, when a breast (not shown in FIG. 1) is placed in the pump head 100 to extract breastmilk, the breastmilk will feed through this feed channel 150, then though a one-way check valve 160 to be collected in a removable collection container 120, such as a baby bottle that can be topped off with a nipple for feeding an infant.

In accordance with preferred embodiments of the illustrated pump head 100, the breast pump is manually operated. In this regard, the user effectuates the extraction of breast milk by manipulating a mechanical actuation device, such as a handle 230, the operation of which is described in more detail below. Although generally described herein with reference to a manual breast pump, the present invention has utility with electric, hydraulic, pneumatic, and other "automatic" breast pumps without departing from the spirit and principles of the present invention.

Referring again to FIG. 1, the neck portion 140 of the pump head 100 includes a top interior surface 170 and a bottom interior surface 175 forming a hollow and nominally cylindrical interior volume adapted to receive a nipple (not shown in FIG. 1) when the user's breast is inserted into the pump head 100. As noted, the neck portion 140 further includes the downward curving portion 130 at its distal end which directs collected breast milk to the feed channel 150. Specifically, the downward curving portion 130 curves at an angle of approximately ninety to one hundred and forty degrees relative to a longitudinal axis of the neck portion 140 and the centerline of the collection container 120. The entire interior surface of the neck section 140, including the downward curving portion 130, is preferably smooth to prevent surface imperfections from irritating the nipple or affecting the extraction and collection of breastmilk. Similarly, the neck portion 140, and especially the downward curving portion 130 is shaped so as not to inhibit breastmilk extraction or collection.

In embodiments of the present invention, a deformable elastic capsule 180, which is preferably filled with an incompressible material 200, such as liquid, gel or the like, but which can also be filled with gas or air, is positioned in an opening or pocket 177 defined in the neck portion 140. As positioned in said opening 177, a first surface 190 of the deformable elastic capsule 180 preferably extends across the opening 177 and faces the interior of the neck portion 140. A second surface 195 faces away from the interior of the neck portion 140. In accordance with embodiments of the present invention, the deformable elastic capsule 180 is preferably hermetically sealed into the neck portion 140.

In embodiments of the present invention, the deformable elastic capsule 180 comprises a single unitary, hermetic unit. In alternate embodiments, the deformable elastic capsule 180 is composed of multiple components, sealed together, and configured to function as a single unitary, hermetic unit. The deformable elastic capsule 180 can comprise a single impermeable polymeric membrane, bladder, a hollow capsule, or the like, sealingly mounted relative to the opening 177 in the neck portion 140 of the pump head 100. In this regard, the deformable elastic capsule 180 may be hermetically bonded between this opening 177 and the sides of the deformable elastic capsule 180 so as to prevent leakage of breastmilk, or loss of suction or pressure from the interior of the pump head 100. As so positioned, and as illustrated in FIG. 1, the first and second surfaces 190 and 195 of the deformable elastic capsule 180 respectively define an exterior bottom surface facing into the neck portion 140 and an exterior top surface facing and/or projecting outside the neck portion 140. The second surface 195 of the deformable elastic capsule 180 exterior to the neck portion 140 is operatively connected to a manual actuator comprising a pushrod 210 which is operatively connected a manual pump handle 230 with a hinge 220.

In the embodiments illustrated in the figures, the deformable elastic capsule 180 is generally positioned on the top of the breast pump 100 and disposed through an opening 177 formed in the top surface 170 of the neck portion 140. In alternate embodiments, the deformable elastic capsule 180 may be positioned relative to the bottom of the breast pump 100 so that it is generally disposed through an opening in the bottom surface 175 of the neck portion, without departing from the spirit and principles of the present invention. In general, reference to the arrangement of the deformable elastic capsule 180 hereinafter is in reference to embodiments with said capsule disposed through the opening 177 on the top surface 170 of the neck portion 140, such that the first surface 190 of the deformable elastic capsule 180 is the "bottom", "lower" and "interior" surface, facing the interior of the neck portion 140, and the second surface 195 of the deformable elastic capsule 180 is the "top", "upper" and "exterior" surface.

In operation of the pump head 100, the breast (not shown in FIG. 1) is inserted into the funnel-shaped breast shield portion 110 and the nipple extends into the receiver neck portion 140. The deformable elastic capsule 180 is preferably in a relaxed state and allows the nipple to enter the neck portion 140 unimpeded. The funnel-shaped portion 110 preferably establishes a seal around the breast.

With the nipple so positioned, the handle 230 of the manual actuator is pushed forward and back by the user (as represented by arrow 240) causing the handle 230 to rotate around a hinge pivot 250 and thereby moving the pushrod 210 away from or toward the interior axial center of the neck portion 140 (this motion being represented by arrow 225 in FIG. 1). The pushrod 210 is operatively connected, and bonded to, the top second surface 195 of the deformable unitary elastic capsule 180. Motion of the pushrod 210 toward the axial center of the neck portion 140 will apply an inwardly directed pressure to the deformable elastic capsule 180 and deform the top second surface 195 thereof outside the neck portion 140. This deformation pressurizes the liquid 200 inside the capsule 180 and causes the bottom first surface 190 of the deformable elastic capsule 180 inside the neck portion 140 to deform toward the axial center of the neck portion 140 (this motion being represented by arrow 260 in FIG. 1), compressing the nipple (not shown in FIG. 1) against the opposing interior solid surface (namely, bottom interior surface 175) of the neck portion 140, thereby controlling nipple edema. Motion of the pushrod 210 away from the axial center of the neck portion 140 will apply an outwardly directed pressure to stretch the top second surface 195 of the deformable unitary elastic capsule 180 outside the neck portion 140. This deformation decreases liquid pressure inside the capsule 180 and causes the bottom first surface 190 of the deformable elastic capsule 180 inside the neck portion 140 to deform away from the axial center of the neck portion 140, thereby creating a volume within the neck portion 130, external to the deformable elastic capsule 180, around and in front of the nipple, to create suction and extract breastmilk. In FIG. 1, the in/out motion of the second surface 195 of the deformable elastic capsule 180 outside the neck portion 140 is represented by arrow 225.

Alternate designs of the mechanical actuation means to apply pressure to and manipulate the deformable elastic capsule can be used without departing from the principles and spirit of the present invention. As generally illustrated in the Figures, a hinged handle 230 and pushrod 210 mechanism is utilized. For example, additional or fewer linkages can be used to provide the push/pull action. In the alternative, a cable can be connected to either or both of the handle 230 and pushrod 210 to effectuate deformation of the capsule.

Figure 2B:
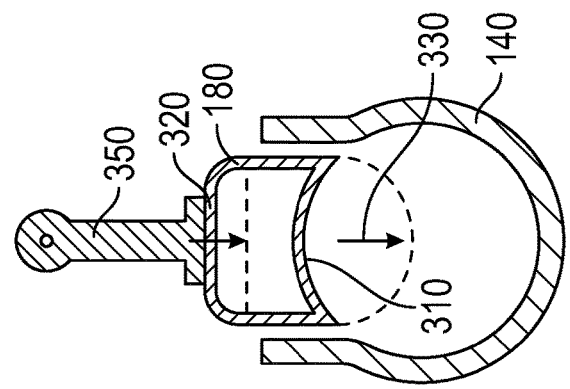
FIGS. 2A and 2B show a planar cross-sectional view and a radial sectional view, respectively, of a portion of the breast pumping head of FIG. 1, illustrating the shape and configuration of a deformable unitary elastic capsule in accordance with embodiments of the present invention.
Figure 2A:
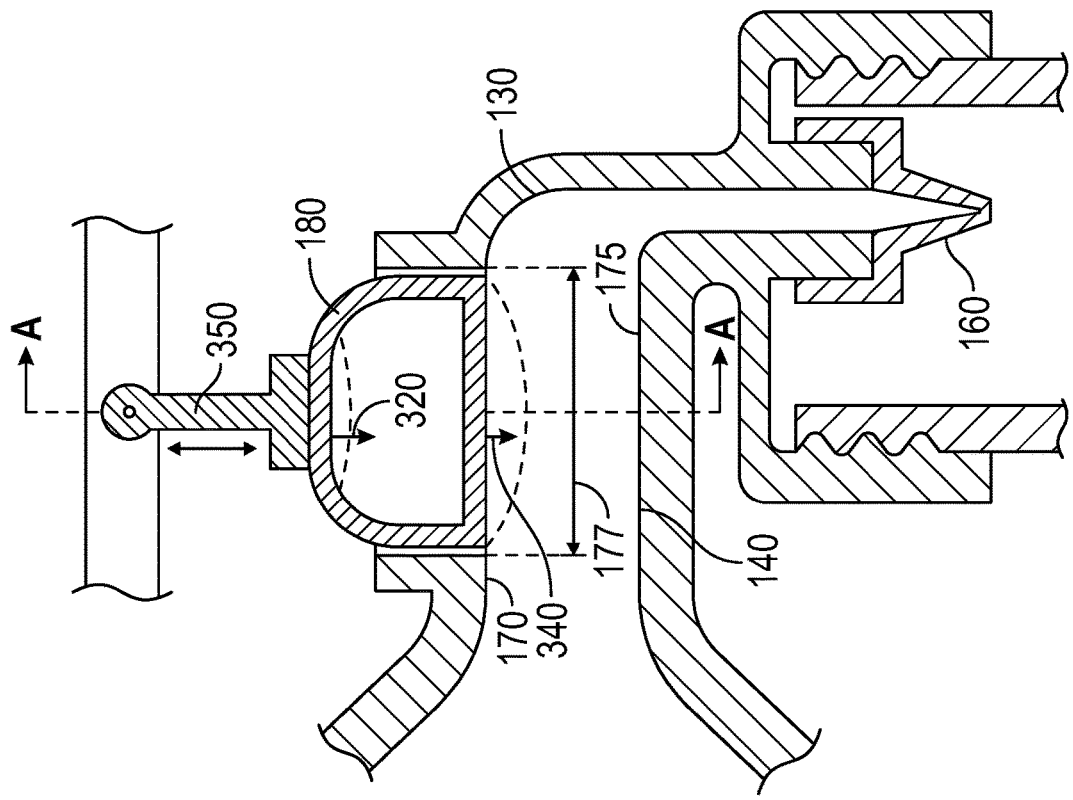

In embodiments of the present invention, a preferred shape of a deformable unitary, hermetic capsule 180 is illustrated in FIGS. 2A and 2B. However, alternate shapes can be used without departing from the principles and spirit of the present invention. As illustrated herein, the deformable unitary, hermetic deformable elastic capsule 180, is positioned in the opening 177 of the neck portion 140 and hermetically bonded between this opening and the side walls of deformable unitary, hermetic deformable elastic capsule 180 so to prevent leakage of breastmilk, pressure or suction from the interior of the pump head 100 when in use. As illustrated, the opening 177 can essentially form a pocket in which the deformable elastic capsule 180 is seated and sealed. As seen in the FIG. 2B, axial view, section A-A, in its relaxed state, the bottom first surface 190 of the deformable elastic capsule 180 facing the interior of the neck portion 140 is concave 310 to roughly follow the nominally cylindrical shape of the neck portion 140. In this regard, the first surface 190 is shaped so that, without deflection, said first surface 190 and the interior surface 170 of the neck portion 140 adjacent thereto form a generally unobstructed cavity within the pump head 100 to receive and position the nipple of the breast.

When the top second surface 195 of the deformable elastic capsule 180 outside the neck portion 140 is mechanically depressed, as shown by arrow 320, and the upper dotted line, by action of the user manipulating the handle 230 (not shown in FIGS. 2A & 2B), and motion of the pushrod 350 deforming the deformable elastic capsule 180 in a direction toward the axial center of the neck portion 140, the bottom first surface 190 of the deformable elastic capsule 180 inside the neck portion 140 deforms inward toward the axial center of the neck portion 140 as shown by arrow 330, and the lower dotted line. In embodiments of the present invention, this inward deformation may be a straightening of the concave surface and/or a bulging 330 of the bottom first surface 190 of the deformable elastic capsule 180, reshaping it from concave to convex, as illustrated by the lower dotted line at 330 in FIG. 2B. There may also be bulging 340 of the bottom first surface 190 of the deformable elastic capsule 180 toward the interior of the neck portion 140 along an axial line, as illustrated by the lower dotted line at 340 in FIG. 2A. In any case, this inward deformation compresses the nipple (not shown in FIG. 2A or 2B) against the opposing interior solid surface 175 of the neck portion 140, thereby controlling nipple edema.

Alternative embodiments for the pump head 100 and deformable elastic capsule 180, as illustrated in FIGS. 3A-3F, include various living hinge configurations disposed between the opening 177 in the neck portion 140 and the capsule 180. It is envisioned that these living hinge configurations would typically be an integral part of, and made from the same material as, the deformable elastic capsule 180. For example, referring to FIG. 3A, the attachment portion of the living hinge is bonded 400 along its sides to the sidewalls 410 that form the opening 177 in the neck portion 140. This bond prevents breastmilk, pressure or suction leakage from the pumping head 100 when in use. The living hinge also allows increased displacement of the capsule 180 beyond simple deformation of its shape.

FIGS. 3A, 3B and 3C each show a single-leaf living hinge. When the pushrod 210 is pushed toward (arrow 420), the axial centerline of the neck portion 140, the living hinge assembly can flex inward, as illustrated by arrow 430 in FIG. 3B, or when the pushrod is pulled away (arrow 440) from the axial centerline of the neck portion 140, the living hinge can flex outward, as illustrated by arrow 450 in FIG. 3C.

FIGS. 3D, 3E and 3F each show a rolling living hinge. When the pushrod 210 is pushed toward (arrow 460 in FIG. 3E), the axial centerline of the neck portion 140, the rolling living hinge can unroll allowing increased inward translation, as illustrated by arrow 470 in FIG. 3E, or when the pushrod 210 is pulled away (arrow 480 in FIG. 3F) from the axial centerline of the neck portion 140, the rolling living hinge can roll up allowing the whole capsule 180 to translate radially outward from the neck portion 140, as illustrated by arrow 490 in FIG. 3F.

Figure 4B:
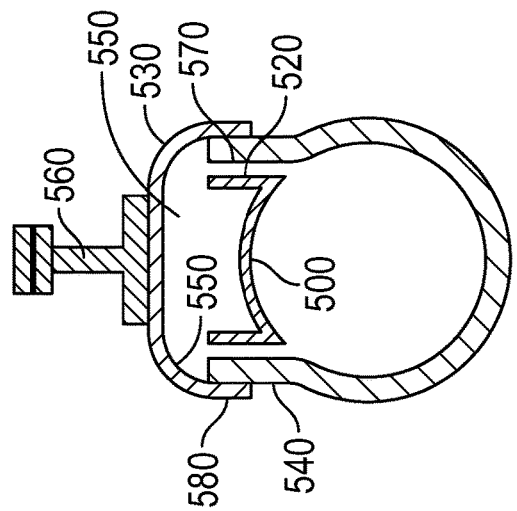
FIGS. 4A and 4B show a planar cross-sectional view and a radial sectional view, respectively, of a portion of a breast pump head in accordance with another embodiment of the present invention, including a neck portion, a deformable composite elastic capsule having, at least, bottom and top polymeric membranes, each hermetically bonded at its sides to the sides of the pocket in the neck portion, a one-way valve, a breastmilk collection container, and further having a handle operatively connected, by a pushrod, to the exterior top surface of the deformable elastic membrane.
Figure 4A:
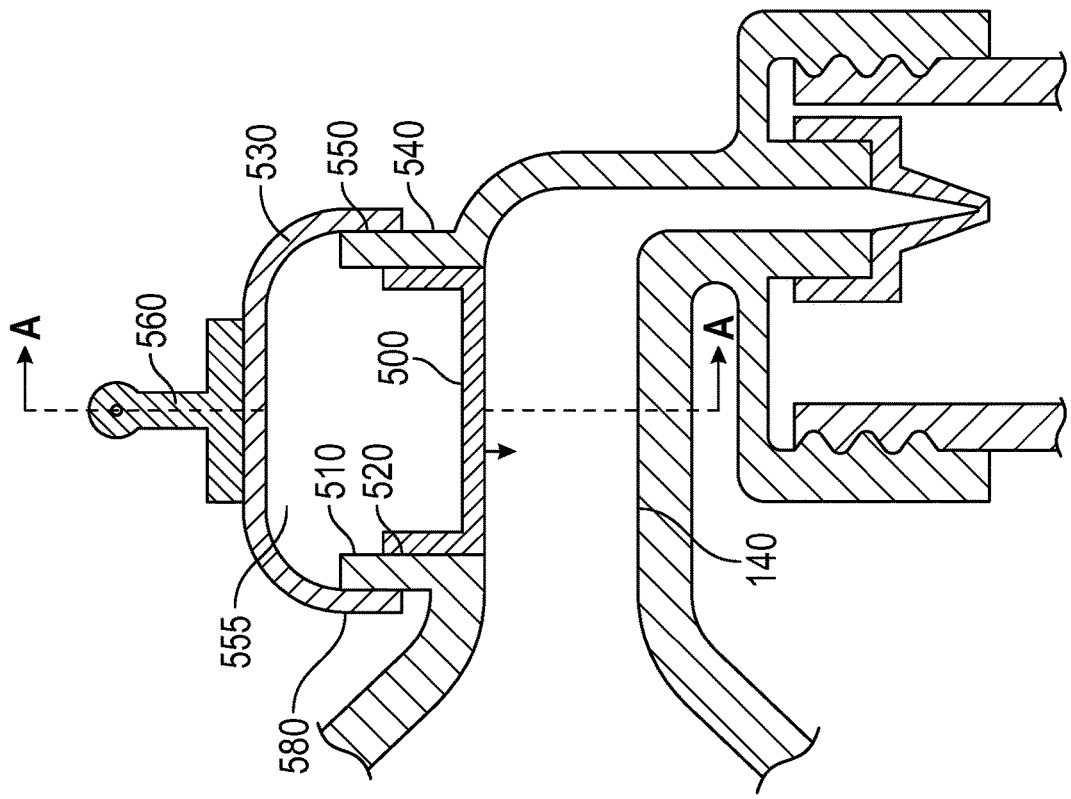

Another alternative embodiment of the present invention for the pump head 100 is shown in FIGS. 4A and 4B. Functionally equivalent to the deformable elastic capsule 180 shown in FIGS. 1 and 2, the illustrated capsule is deformable, and hermetic but is not unitary, instead it is composed of a composite structure. Referring to FIG. 4A, the outside walls 520 of a deformable impermeable polymeric membrane 500 are bonded to the inside walls 510 of a pocket that forms an opening 177 in the neck portion 140 to form a hermetic seal so as to prevent leakage of breastmilk, or loss of suction or pressure from the interior of the pump head 100. The inside walls 550 of another deformable impermeable polymeric membrane 530 are bonded to the outside walls 540 of the pocket that forms an opening 177 of the neck portion 140 to form a hermetic seal between the composite capsule and the neck portion 140. An alternate structure would be to bond the outside walls 580 of the upper membrane 530 to the inside walls 510 of the pocket that forms the opening 177 in the neck section 140. Thus, the composite structure composed of the bottom membrane 500, the pocket having inside 510 and outside 540 walls and the top membrane 530 forms a composite capsule that is hermetic but not unitary. As with the capsule designs in FIGS. 1A and 2A, the interior of the composite capsule in FIG. 4A is preferably filled with an incompressible material 555, such as liquid, gel, or the like.

The top membrane 530 of the deformable, hermetic composite capsule is deformed by up/down action of a pushrod 560 which is bonded to it and is operatively connected to a handle (not shown in FIG. 4A). Deformation of the top membrane 530 causes corresponding deformation of the bottom membrane 500 which either creates suction in the neck portion 140 or compresses the nipple (not shown in FIG. 4A). Both actions are functionally equivalent to the action of the deformable, unitary and hermetic elastic capsule embodiments as described above and pictured in FIGS. 1A and 2A.

Figure 5B:
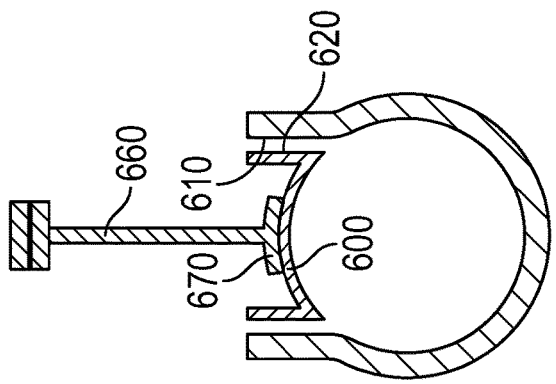
FIGS. 5A and 5B show a planar cross-sectional view and a radial sectional view, respectively, of a portion of a breast pump head in accordance with another embodiment of the present invention, including a neck portion, a deformable impermeable polymer membrane hermetically bonded at its sides to the sides of the pocket in the neck portion, a one-way valve, a breastmilk collection container, and further having a handle operatively connected, by a pushrod, to the exterior surface of the deformable polymer membrane.
Figure 5A:
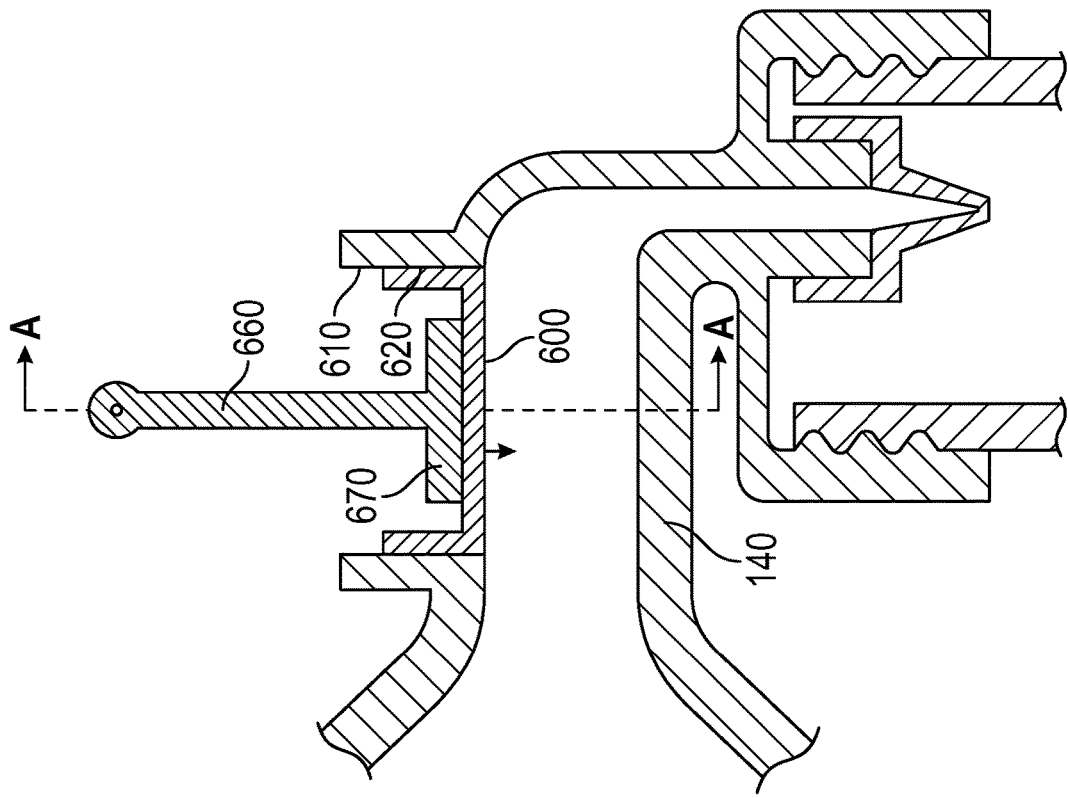

Another alternate embodiment of the present invention for the pumping head 100 is shown in FIGS. 5A and 5B. As illustrated, the outside walls 620 of a deformable impermeable polymeric membrane 600 are bonded to the inside walls 610 of a pocket that forms the opening 177 in the neck portion 140 to form a hermetic seal between these inside walls 610 and the outside walls 620 of the deformable elastic component 600 so as to prevent leakage of breastmilk, or loss of suction or pressure from the interior of the pumping head 100. The top surface of membrane 600 is deformed by up/down action of a pushrod 660 which is bonded to it and is operatively connected to a handle (not shown in FIG. 5A). Pressure of the pushrod 660 is distributed over the top surface of membrane 600 by a presser foot 670 which is an integral part of pushrod 660. The presser foot 670 is bonded to the top surface of the polymer membrane 600. Downward motion of pushrod 660 will cause membrane 600 to deform toward the axial center of the neck portion 140 compressing the nipple (not shown in FIG. 5A) against the opposing interior solid surface 175 of the neck portion 140, thereby controlling nipple edema. Upward motion of the pushrod 660 away from the axial center of the neck portion 140 will retract the elastic membrane 600 thereby creating a volume within the neck portion 140, external to membrane 600, around and in front of the nipple, to create suction and extract breastmilk.

Figure 6B:
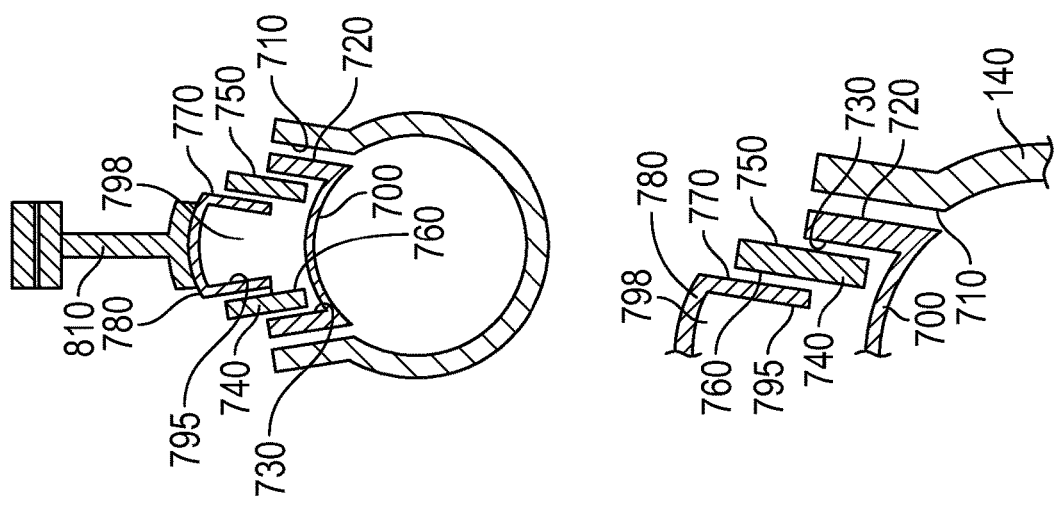
FIGS. 6A and 6B show a planar cross-sectional view and a radial sectional view, respectively, of a portion of a breast pump head in accordance with another embodiment of the present invention, including a neck portion, a detachable deformable composite capsule hermetically pressure-sealed at its sides into a tapered pocket in the neck portion, a one-way valve, a breastmilk collection container, and further having a handle operatively connected, by a pushrod, to the exterior top surface of the deformable polymer membrane.
Figure 6A:
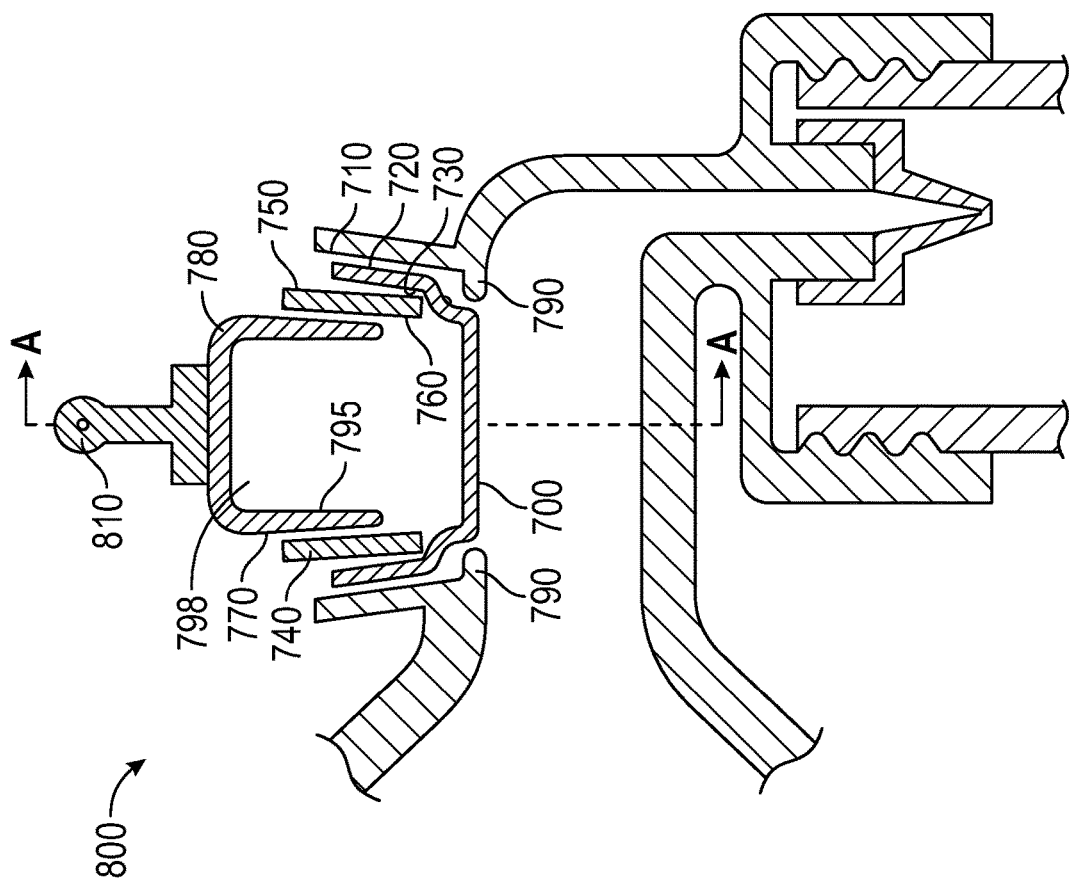

Another alternative embodiment of the present invention for the pump head 100 is shown in FIGS. 6A and 6B. Functionally equivalent to the deformable elastic capsule shown in FIGS. 1A, 2A and 4A, this composite capsule is deformable, and hermetic but also detachable from the pump head 100 for removal and reinsertion, which may facilitate cleaning of the pump head 100. As illustrated in FIGS. 6A and 6B, the inside walls 710 of the pocket that forms the opening 177 in the neck portion 140 are tapered outward, essentially forming a 4-sided pyramidal opening. The outside walls 720 of the lower deformable impermeable polymer membrane 700 are tapered to the same angle as the inside walls 710 of the pocket. Conforming to the shape of the inside walls 730 of the lower deformable impermeable polymer membrane 700 is a rigid form 740. The outside walls 750 of this rigid form 740 are bonded to the inside walls 730 of the lower deformable impermeable polymer membrane 700. The inside walls 760 of the rigid form 740 are bonded to the outside walls 770 of the upper deformable impermeable polymer membrane 780. An alternate structure would be to bond the inside walls 795 of the upper deformable impermeable polymer membrane 780 to the outside walls 750 of the rigid form 740. After bonding, a hermetic composite capsule is formed ("hermetic composite capsule", has the same meaning as in the description accompanying FIG. 4A, above). The interior 798 of the hermetic, composite capsule is preferably filled with an incompressible material, such as liquid, gel, or the like, though it may also be filled with a gas or air.

To attach the tapered hermetic composite capsule 800 to the pump head 100, the capsule 800 is pushed into the tapered opening of the pocket that forms the opening 177 in the neck portion 140 until the capsule 800 comes up against the lower stop 790, which radially positions the composite capsule 800 in the neck portion 140. The seal is effectuated by the elastic polymer walls of the lower polymer membrane 700 being forced out by the rigid form 740 inside and thereby sealing the composite capsule 800 into the tapered opening. In operation, up/down motion of the pushrod 810 (which is bonded to the top of the upper polymer membrane 780) causes up/down deformation of the upper polymer membrane 780. This respectively decreases or increases pressure of a liquid or gel 798 disposed inside the capsule 800, which causes the lower impermeable polymer membrane 700 to deform away from or into the neck portion 140, respectively causing suction in the neck portion 140 or compression of the nipple (not shown in FIG. 6A). The embodiment illustrated in FIG. 6A, and the associated description herein, relate to just one example of a removable capsule. It will be understood by those skilled in the art that other forms and details are possible without departing from the spirit and scope of the present invention.

Thought the deformable elastic capsule in accordance with the present invention is general illustrated and described herein as a "capsule", the deformable elastic component may also comprise an impermeable polymeric membrane sealed into the neck portion 140 and defining a first surface 190 inside or facing the interior of the neck portion 140 and a second surface 195 exterior to or facing away from the interior of the neck portion 140.

In another embodiment, the entire interior surface of pump head 100 may be covered with a highly elastic material to form a membrane which covers the inside of funnel-shaped shield portion 110, neck portion 140, feed channel 150 and the surface of the various deformable elastic components facing into the neck portion 140. Such an elastic membrane will allow full and unrestricted expansion and contraction functioning of the deformable elastic components while preventing breastmilk collection in small spaces inside the pump head 100. In another embodiment this highly elastic membrane may be removable and reusable or may be a disposable item. All such configurations will ease cleaning.

During manual pumping using the pump head 100, breastmilk is directed through the feed channel 150 and one-way check valve 160, and thereafter collected in the collection container 120. Preferably, the one-way check valve is disposed between the neck portion 140 and the collection container 120 to prevent air leakage from the collection container 120 into the feed channel 150. Additionally, the collection container 120 is attachable to a connection portion, preferably threaded, formed on the feed channel 150 to form a seal serving to prevent breastmilk leakage from the collection container 120 when the pump head 100 is tipped. An air vent may further be provided to allow the release of air from the collection container 120 as breastmilk is pumped into said container 120. In preferred embodiments, the air vent is located at a position upstream from the connection portion to reduce likelihood that breastmilk will leak through the air vent when the pump head 100 is tipped.

In preferred designs, the axial centerline of the collection container 120 is offset relative to the axial centerline of the one-way check valve 160. Further, the axial centerline of the collection container 120 can be oriented between about a ninety and a one hundred forty-degree angle relative to the axial center of the neck portion.

When the pumping session is complete, the user can insert a finger into funnel-shaped portion 110 and possibly into the receiver neck portion 140 and break the residual suction between the breast and the funnel-shaped shield portion 110. Breastmilk collected in the collection container 120 can be fed to an infant or stored for future use.

The one-way check valve 160 can be removed to facilitate cleaning the pump head 100. Any residual breastmilk can be removed from the interior of the funnel-shaped breast shield portion 110 and the receiver neck portion 140 via a brush with soap, detergent and warm water.

Additionally, the features of the present invention may also be used for milking machines. Specifically, the above described methods and pump head 100 may be used for the milking of animals.

Although the present invention has been shown and described with respect to the detailed embodiments thereof, it will be understood by those skilled in the art that various changes in form and detail thereof may be made without departing from the spirit and scope of the invention.

It is noted that the Figures are to be taken as an illustrative example only and are not to scale.

Additionally, it is also to be understood that the terminology used if for the purpose of describing particular embodiments only and is not intended to limit the scope of the claims of the present invention.

What is claimed is:

1. A device for extracting breastmilk from a breast, said device comprising:
   an external shell including:
      a funnel-shaped portion configured to receive and seal against the breast;
      a neck portion extending from the funnel-shaped portion and defining a proximal end and a distal end, said neck portion being adapted to receive and position a nipple of the breast, and
      a feed channel defined at the distal end of the neck portion; and
   a deformable elastic component sealed into the neck portion and comprising a first surface facing an interior of the neck portion, a second surface exterior to the neck portion and facing away from the interior of the neck portion, and a cavity disposed between the first surface and the second surface and being enclosed by the first and second surface;
   wherein the first surface of the deformable elastic component is configured to deform into an interior volume of the neck portion when pressure is applied to the second surface exterior to the neck portion to move the second surface, and in a direction toward an axial center of the neck portion such that the first surface of the deformable elastic component compresses the nipple to control nipple edema, and
   wherein the first surface of the deformable elastic component is configured to deform away from the interior of the neck portion when pressure is applied to the second surface of the deformable elastic component exterior to the neck portion to move the second surface, and in a direction away from the axial center of the neck portion to create a volume within the neck portion, external to the deformable elastic component, around and in front of the nipple, to create suction and extract breastmilk.

2. The device according to claim 1, wherein the first surface of the deformable elastic component is shaped so that, without deflection, said surface and an interior surface of the neck portion adjacent thereto form a generally unobstructed cavity to receive and position the nipple of the breast.

3. The device according to claim 1, Wherein pressure is applied to the second surface of the deformable elastic component in a direction either toward or away from the axial center of the neck portion by a mechanical means which is manually controlled by the user.

4. The device according to claim 3, wherein the mechanical means comprises a handle and a pushrod interposed between said handle and the second surface of the deformable elastic component, wherein said handle can be manipulated by the user to apply pressure to the second surface in direction either toward or away from the axial center of the neck portion via the pushrod.

5. The device according to claim 1, wherein the deformable elastic component comprises a single impermeable polymeric membrane sealed into the neck portion and defining the first surface facing an interior of the neck portion and the second surface exterior to the neck portion.

6. The device according to claim 1, wherein the deformable elastic component comprises a hollow capsule sealingly mounted within an opening in the neck portion such that the first surface is positioned facing the interior of the neck portion.

7. The device according to claim 6, wherein the capsule comprises a single unitary, hermetic unit.

8. The device according to claim 6, Wherein the capsule is composed of multiple components sealed together and configured to function as a single unitary, hermetic unit.

9. The device according to claim 6, wherein the capsule is filled with one of a liquid, a gel or a gas.

10. The device according to claim 6, wherein the capsule is detachable from the neck portion.

11. The device according to claim 6, wherein a flexible element is disposed between, and hermetically sealed to the hollow capsule and the neck portion such that when pressure is applied to a second surface of the hollow capsule in a direction either towards or away from the axial center of the neck portion, the entire hollow capsule can move in a direction either towards or away from the axial center of the neck portion, thereby increasing deflection of the first surface of the hollow capsule.

12. The device according to claim 1, further including a collection container connected to the feed channel to receive breastmilk.

13. A milking machine for extracting milk from a breast comprising:
an external shell including:
a funnel-shaped portion configured to receive and seal against a breast;
a neck portion extending from the funnel-shaped portion and defining a proximal end and a distal end, said neck portion being adapted to receive and position a nipple of the breast; and
a feed channel defined at the distal end of the neck portion;
a deformable elastic component sealed into the neck portion comprising a first surface facing an interior of the neck portion, a second surface exterior to the neck portion and facing away from the interior of the neck portion, and a cavity disposed between the first surface and the second surface and being enclosed by the first and second surface; and
a mechanical actuation device, controlled by the user, operatively connected to the second surface of the deformable elastic component;
wherein, under pressure applied to the second surface of the deformable elastic component in a direction toward an axial center of the neck portion to move the second surface, the first surface of the deformable elastic component is configured to deform inwardly toward the axial center of the neck portion such that the first surface of the deformable elastic component compresses the nipple to control nipple edema, and
wherein, under pressure applied to the second surface of the deformable elastic component in a direction away from the axial center of the neck portion to move the second surface, the first surface of the deformable elastic component is configured to deform outwardly, away from the axial center of the neck portion to create a volume within the neck portion, external to the deformable, elastic component, around and in front of the nipple, to create suction and extract breastmilk.

14. The milking machine according to claim 13, wherein the deformable elastic component comprises a single impermeable polymeric membrane sealed into the neck portion and defining the first surface facing an interior of and the second surface exterior to the neck portion.

15. The milking machine according to claim 13, wherein the deformable elastic component comprises a hollow capsule sealingly mounted within an opening in the neck portion.

16. The milking machine according to claim 15, wherein the capsule comprises a single unitary, hermetic unit.

17. The milking machine according to claim 15, wherein the capsule is composed of multiple components sealed together and configured to function as a single unitary, hermetic unit.

18. The milking machine according to claim 15, wherein the deformable elastic capsule is filled with one of a liquid, a gel or a gas.

19. The milking machine according to claim 15, wherein a flexible element is disposed between, and hermetically sealed to the hollow capsule and the neck portion such that when pressure is applied a second surface of the hollow capsule in a direction either towards or away from the axial center of the neck portion, the entire hollow capsule can move in a direction either towards or away from the axial center of the neck portion, thereby increasing deflection of the first surface of the hollow capsule.

20. The milking machine according to claim 13, further comprising a collection container connected to the feed channel to receive breastmilk.

* * * * *